United States Patent [19]

Carmichael et al.

[11] Patent Number: 5,990,298
[45] Date of Patent: Nov. 23, 1999

[54] CIS-ACTING CELLULAR NUCLEIC ACID MOLECULES

[75] Inventors: Gordon G. Carmichael, West Hartford; Yinggun Huang, New Britain, both of Conn.

[73] Assignee: The University of Connecticut, Farmington, Conn.

[21] Appl. No.: 08/928,562

[22] Filed: Sep. 12, 1997

[51] Int. Cl.$^6$ ..................................................... C07H 21/04
[52] U.S. Cl. ..................... 536/24.1; 435/69.1; 435/69.2; 435/440; 435/455; 435/375; 435/320.1; 536/23.1
[58] Field of Search .................................. 435/69.1, 69.2, 435/440, 455, 375, 320.1; 436/501; 536/23.1, 24.1

[56] References Cited

U.S. PATENT DOCUMENTS

| | | | |
|---|---|---|---|
| 5,585,263 | 12/1996 | Hammarskjöld et al. | 435/236 |
| 5,686,120 | 11/1997 | Mertz et al. | 435/320.1 |

OTHER PUBLICATIONS

Cullen, B.R., "Mechanism of Action of Regulatory Proteins Encoded by Complex Retroviruses", *Microbiol. Rev.* 56 (*3*): 375–394 (1992).

Bray, M., et al., "A small element from the Mason–Pfizer monkey virus genome makes human immunodeficiency virus type 1 expression and replication Rev–independent", *Proc. Natl. Acad. Sci. USA*, 91:1256–1260 (1994).

Yen, T.S., "Regulation of hepatitis B virus gene expression", *Virology* 4:33–42 (1993).

McKnight, S.L., "The nucleotide sequence and transcript map of the herpes simplex virus thymidine kinase gene", *Nucleic Acids Research*, 8(24):5949–5964 (1980).

Liu and Mertz, "HnRNP L binds a cis–acting RNA sequence element that enables intron–independent gene expression", *Genes & Development*, 9:1766–1780 (1995).

Donello, J.E., et al., "The Hepatitis B Virus Posttranscriptional Regulatory Element Is Composed of Two Subelements", *J. Virol.*, 70(7):4345–4351 (1996).

Huang and Liang, "A Novel Hepatitis B Virus (HBV) Genetic Element with Rev Response Element–Like Properties That Is Essential for Expression of HBV Gene Products", *Mol. Cell. Biol.* 13(12):7476–7486 (1993).

Huang and Yen, "Role of the Hepatitis B Virus Posttranscriptional Regulatory Element in Export of Intronless Transcripts", *Mol. Cell. Biol.*, 15(7):3864–3869 (1995).

Kedes. L.H., "Histone Genes and Histone Messengers", *Ann. Rev. Biochem.*, 48:837–870 (1979).

Kobilka, B.K. et al., "An intronless gene encoding a potential member of the family of receptors coupled to guanine nucleotide regulatory proteins", *Nature*, 329:75–79 (1987).

Nagata, S., et al., "The structure of one of the eight or more distinct chromosomal genes for human interferon–α", *Nature*, 287:401–408 (1980).

Hattori, K., et al., "Structure and chromosomal localization of the functional intronless human JUN protooncogene", *Proc. Natl. Acad. Sci. USA* 85:9148–9152 (1988).

Hentschel and Birnstiel, "The Organization and Expression of Histone Gene Families", *Cell* 25:301–313 (1981).

Malim and Cullen, "Rev and the Fate of Pre–mRNA in the Nucleus:Implications for the Regulation of RNA Processing in Eukaryotes", *Mol. Cell. Biol.*, 13(10):6180–6189 (1993).

(List continued on next page.)

*Primary Examiner*—Ardin H. Marschel
*Attorney, Agent, or Firm*—Hamilton, Brook, Smith & Reynolds, P.C.

[57] ABSTRACT

An isolated cis-acting cellular nucleic acid molecule from a histone gene which suppresses splicing and facilitates transport of unspliced RNA and RNA from intronless DNA from a cell nucleus to the cytoplasm of the cell is described, as well as expression vectors and recombinant host cells containing the nucleic acid molecule and methods of use therefor.

19 Claims, 7 Drawing Sheets

OTHER PUBLICATIONS

Bogerd, H.P., et al., "Identification of a Novel Cellular Cofactor for the Rev/Rex Class of Retroviral Regulatory Proteins", *Cell,* 82:485–494 (1995).

Fischer, U., et al., "The HIV–1 Rev Activation Domain Is a Nuclear Export Signal That Assesses an Export Pathway Used by Specific Cellular RNAs", *Cell,* 82:475–483 (1995).

Fritz, C.C., et al., "A Human nucleoporin–like protein that specifically interacts with HIV Rev", *Nature,* 376:530–533 (1995).

Huang and Carmichael, "Role of Polyadenylation in Nucleocytoplasmic Transport of mRNA", *Mol. Cell. Biol.* 16(4):1534–1542 (1996).

Eckner, R., et al., "Mature mRNA 3' end formation stimulates RNA export from the nucleus", *EMBO J.,* 10 (11):3513–3522 (1991).

Williams, A.S., et al., "Changes in the stem–loop at the 3' terminus of histone mRNA affects its nucleocytoplasmic transport and cytoplasmic regulation", *Nucleic Acids Research,* 22(22):4660–4666 (1994).

Liu and Mertz, "Sequence of the polypyrimidine tract of the 3'—terminal 3' splicing signal can affect intron–dependent pre–mRNA processing in vivo", *Nucleic Acids Research,* 24(9):1765–1773 (1996).

Dargemont and Kühn, "Export of mRNA from Microinjected Nuclei of *Xenopus laevis* Oocytes", *J. Cell Biol.,* 118(1):1–9 (1992).

Hamm and Mattaj, "Monomethylated Cap Structures Facilitate RNA Export from the Nucleus", *Cell,* 63:109–118 (1990).

Izaurralde, E., et al., "A Cap Binding Protein That May Mediate Nuclear Export of RNA Polymerase II–transcribed RNAs", *J. Cell Biol.,* 118 (6):1287–1295 (1992).

Harris, M.E., et al., "Regulation of Histone mRNA in the Unperturbed Cell Cycle: Evidence Suggesting Control at Two Posttranscriptional Steps", *Mol. Cell. Biol.,* 11(5):2416–2424 (1991).

Hammarskjöld, M–L, "Regulation of retroviral RNA export", *Cell & Develop. Biol.* 8:83–90 (1997).

Buchman and Berg, "Comparison of Intron–Dependent and Intron–Independent Gene Expression", *Mol. Cell. Biol.* 8(10):4395–4405 (1988).

```
mRNA Starts
                                                        Start
                                                        Codon
CGGAGTACCGTTTCCTGGTTGTGCCGTTCGTCTGTTTGCGCTTTCGTGC ATG TCCGGTCGTGTGGCAAGCAAGGAGGCAAGGC    80
GCCTCATGGCAAAGACCAACACCGGCAAGCAGACAAGCACGTACAGGCCGAAAACGCACGTACAGGCCGAAAAGCACGTTCCTCCGTTCCG CCGCGCCAAGGCCAAGTCGCGGTCTTCCCGGCCGGCTACAGTTCCCGGTGGGGCGTGTGCACCGGCTGCTCGCGAAGG             160
GGCGCGGTTCCGGTTCAGCGCCGGCCACCCGGCCCGGCCTGATGTCAAGGGCCACACACGTGGCCGACGACGCCTTCC GCAACTACGCGGAGCGCGTGGGCGCGGCGCGCCCCGGTATA CATGGGGCGCGGTGCTGAGTACCTAAGGCCGAGATCCTG          240
CGTTGATGCGCCTCGCGCACCCGCCGCCGCCGGCCCCATAT GTACCGCCGCCACGACCTCATGGATTGCCGGCTCTAGGAC
                                      201

GAGCTGGGCGGGGCAACGCGCCCCGCAACAAGAGAACGCGCATCATCCCGCCACCTGC AGCTGGCCATCCGCAACGA  320
        CTCGACCCGCCCGTTGCCGCGGGCGCTGTTGTTCTCTGCGCGTAGGCGCGGTGGACG TCGACCGGTAGGCGTTGCT
                                                                301

CGAGGAGCTCAACAAGCTGCTGGGCAAAGTGACGATCGCGCAGGCGGCGCTCTGCCCAACATCCAGGCCGTGCTGCTGC            400
GCTCCTCGAGTTGTTCGACGACCCGTTCACTGCTAGCGCGTCCCGCCGCGACGGGTTGTAGGTCCGGCACGACGACG

Stop
                                                  Codon
CCAAGAAGACGGAGAGCCACCATAAGGCGAAGGGCAAG TGA GCCACTGCTCGCGCTCCGGCCCCGCGTCTCTGTGATATAAC        480
GGTTCTTCTGCCTCTCGGTGGTATTCCGCTTCCCGTTCACT ACT CGGTGACGAGCGCGAGCCGGGCGCAGAGACACTATATTG CCCCGCGAGCTCCCAAAAAGGCTCTTTTCAGAGCC         515
GGGGCGCTCGAGGGTTTTTCCGAGAAAAGTCTCGG          mRNA ends
 496

(SEQ ID NOS. 1 and 2)
```

FIG. 6

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 517 base pairs
      (B) TYPE: nucleic acid
      (C) STRANDEDNESS: single
      (D) TOPOLOGY: linear    (ix) FEATURE:
      (A) NAME/KEY: Coding Sequence
      (B) LOCATION: 51...440
      (D) OTHER INFORMATION:

(xi) SEQUENCE DESCRIPTION: SEQ ID NO:1:

```
CGGAGTACCG TTTCCTGGTT GTGGCCGTTC GTCTGTTTGC GCTTTCGTGC ATG TCC        56
                                                      Met Ser
                                                        1

GGT CGT GGC AAG CAA GGA GGC AAG GCC CGC GCC AAG GCC AAG TCG CGG      104
Gly Arg Gly Lys Gln Gly Gly Lys Ala Arg Ala Lys Ala Lys Ser Arg
          5                  10                  15

TCT TCC CGG GCC GGG CTA CAG TTC CCG GTG GGG CGT GTG CAC CGG CTG      152
Ser Ser Arg Ala Gly Leu Gln Phe Pro Val Gly Arg Val His Arg Leu
     20                  25                  30

CTG CGG AAG GGC AAC TAC GCG GAG CGC GTG GGC GCC GGC GCG CCG GTA      200
Leu Arg Lys Gly Asn Tyr Ala Glu Arg Val Gly Ala Gly Ala Pro Val
 35                  40                  45                  50
```

```
TAC ATG GCG GCG GTG CTG GAG TAC CTA ACG GCC GAG ATC CTG GAG CTG         248
Tyr Met Ala Ala Val Leu Glu Tyr Leu Thr Ala Glu Ile Leu Glu Leu
            55                  60                  65

GCG GGC AAC GCG GCC CGC GAC AAC AAG AAG ACG CGC ATC ATC CCG CGC         296
Ala Gly Asn Ala Ala Arg Asp Asn Lys Lys Thr Arg Ile Ile Pro Arg
        70                  75                  80

CAC CTG CAG CTG GCC ATC CGC AAC GAC GAG GAG CTC AAC AAG CTG CTG         344
His Leu Gln Leu Ala Ile Arg Asn Asp Glu Glu Leu Asn Lys Leu Leu
            85                  90                  95

GGC AAA GTG ACG ATC GCG CAG GGC GGC GTC CTG CCC AAC ATC CAG GCC         392
Gly Lys Val Thr Ile Ala Gln Gly Gly Val Leu Pro Asn Ile Gln Ala
        100                 105                 110

GTG CTG CTG CCC AAG AAG ACG GAG AGC CAC CAT AAG GCG AAG GGC AAG         440
Val Leu Leu Pro Lys Lys Thr Glu Ser His His Lys Ala Lys Gly Lys
115                 120                 125                 130

TGAGGCCACT GCTCGCGTCG GCCCGCGTCT CTGTGATATA ACCCCCGCGA GCTCCCAAAA       500

AGGCTCTTTT CAGAGCC                                                      517

(2) INFORMATION FOR SEQ ID NO:2:

(i) SEQUENCE CHARACTERISTICS:
        (A) LENGTH: 517 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

GCCTCATGGC AAAGGACCAA CACCGGCAAG CAGACAAACG CGAAAGCACG TACAGGCCAG         60

CACCGTTCGT TCCTCCGTTC CGGGCGCGGT TCCGGTTCAG CGCCAGAAGG GCCCGGCCCG        120

ATGTCAAGGG CCACCCCGCA CACGTGGCCG ACGACGCCTT CCCGTTGATG CGCCTCGCGC        180

ACCCGCGGCC GCGCGGCCAT ATGTACCGCC GCCACGACCT CATGGATTGC CGGCTCTAGG        240

ACCTCGACCG CCCGTTGCGC CGGGCGCTGT TGTTCTTCTG CGCGTAGTAG GGCGCGGTGG        300

ACGTCGACCG GTAGGCGTTG CTGCTCCTCG AGTTGTTCGA CGACCCGTTT CACTGCTAGC        360

GCGTCCCGCC GCAGGACGGG TTGTAGGTCC GGCACGACGA CGGGTTCTTC TGCCTCTCGG        420

TGGTATTCCG CTTCCCGTTC ACTCCGGTGA CGAGCGCAGC CGGGCGCAGA GACACTATAT        480

TGGGGGCGCT CGAGGGTTTT TCCGAGAAAA GTCTCGG                                 517
```

CIS-ACTING CELLULAR NUCLEIC ACID MOLECULES

GOVERNMENT SUPPORT

Work described herein was supported by Grant Number CA45382 from the National Institutes of Health. The U.S. Government has certain rights in the invention.

BACKGROUND OF THE INVENTION

In eukaryotic cells, most transcripts synthesized by RNA polymerase II contain introns that are removed by splicing before transport to the cytoplasm. Unspliced mRNAs are usually excluded from the cytoplasm. Although the molecular basis for the nuclear retention of unspliced transcripts is generally unclear, it seems likely that either the process of splicing positively affects RNA transport, or the presence of spliceosomes on transcripts negatively affects RNA export from the nucleus. Based on experiments in a yeast system, it has been proposed that intron-containing mRNAs are retained in the nucleus due to association with spliceosomes (Legrain & Rosbash, Cell 57:573-583 (1989)). In mammalian systems, similar observations have been made. Chang and Sharp reported enhanced cytoplasmic accumulation of unspliced mRNAs when splice sites present in nascent transcripts were incapable of efficient spliceosome formation (Chang & Sharp, Cell 59:789-795 (1989)).

Splicing is not always a prerequisite for efficient cytoplasmic accumulation of mRNAs. In retroviruses, for example, alternative splicing of a single viral pre-mRNA generates multiple RNA products, a significant fraction of which are partially spliced or fully unspliced. These intron-containing mRNAs encode viral structural proteins, and their cytoplasmic accumulation is essential for the viral life cycle. In the case of HIV-1, efficient cytoplasmic accumulation of singly spliced and unspliced viral mRNAs requires a viral regulatory protein, called Rev, which interacts with the Rev-responsive element (RRE) present in the target transcripts (reviewed in Cullen, Microbiol. Rev. 56:375-394 (1992)). However, HIV RRE only works in some cell types; for example, it does not work in mouse cells.

For simple retroviruses, such as the Mason-Pfizer monkey virus, cytoplasmic localization of unspliced viral mRNAs involves the interaction of a cis-acting RNA element with an unidentified cellular factor(s) (Bray et al., Proc. Natl. Acad. Sci. USA 91:1256-1260 (1994)). Thus, specific interactions between positive cis-acting RNA elements and appropriate viral or cellular factors appear to facilitate the cytoplasmic accumulation of intron-containing retroviral mRNAs.

Some viral genes naturally lack introns. Examples include the hepatitis B virus (HBV) (reviewed in Yen, Semin. Virol. 4:33-42 (1993)) and the herpes simplex virus thymidine kinase (HSV-TK) (McKnight, Nucleic Acids Res. 8:5949-5964 (1980)) genes. Unlike the intronless variants of the highly intron-dependent gene transcripts that usually fail to accumulate in the cytoplasm (Jonsson et al., Nucleic Acids Res. 20:3191-3198 (1992); Nesic et al., Mol. Cell. Biol. 13:3359-3369 (1993); Neuberger & Williams, Nucleic Acids Res. 16:6713-6724 (1988)), these intronless viral transcripts can efficiently accumulate in the cytoplasm without undergoing the process of splicing (Yen, Semin. Virol. 4:33-42 (1993); McKnight, Nucleic Acids Res. 8:5949-5964 (1980); Liu & Mertz, Genes Dev. 9:1766-1780 (1995)). Recent studies have indicated that the cytoplasmic accumulation of unspliced HBV transcripts is facilitated by a specific cis-acting RNA element that interacts with cellular factors (Donello et al., J. Virol. 70:4345-4351 (1996); Huang & Liang, Mol. Cell. Biol. 13:7476-86 (1993); Huang & Yen, Mol. Cell. Biol. 15:3864-3869 (1995)).

In contrast to viral intronless gene expression, much less is known about the expression of cellular intronless genes, which include the genes coding for histone proteins (Kedes, Annu. Rev. Biochem. 48:837-870 (1979)), β-adrenergic receptor (Koilka et al., Nature 329:75-79 (1987)), α-interferon (Nagata et al., Nature 287:401-408 (1980)) and c-jun (Hattori et al., Proc. Natl. Acad. Sci. USA 85:9148-9152 (1988)). The existence of a cis-acting element in the c-jun message has been suggested (unpublished results, cited in Liu & Mertz, Genes Dev. 9:1766-1780 (1995)).

In many applications, e.g., in research laboratories, transgenic research and gene therapy, genes are expressed from vectors that are designed to make large amounts of the desired mRNA. In a common formulation, a DNA segment obtained by making a complementary copy of a desired mRNA (a cDNA molecule) is inserted into an expression vector downstream of a promoter and just upstream of a polyadenylation signal. Frequently, when this is done in its simplest form, very little expression is observed because much or most gene expression in eukaryotic cells appears to require the splicing of introns in order to allow cytoplasmic accumulation of mRNA. While the reason for this almost general requirement for splicing is unclear, most expression vectors attempt to alleviate this problem by incorporating an intron either upstream or downstream of the coding region contained in the DNA insert. One of the most commonly used introns is the SV40 small t antigen intron. However, this intron can lead to aberrant splicing, and splicing to "cryptic" sites lying within the cDNA of interest (Huang and Gorman, Mol. Cell. Biol. 10:1805-1810 (1990)), resulting in lower than optimal levels of mRNA.

SUMMARY OF THE INVENTION

Histone mRNAs are naturally intronless and accumulate efficiently in the cytoplasm. To learn whether there are cis-acting sequences within histone genes that allow efficient cytoplasmic accumulation of RNAs, recombinant constructs were made in which sequences from the mouse H2a gene were cloned into a human β-globin cDNA. Using transient transfection and RNAse protection analysis, it was demonstrated as described herein that a 101-base pair sequence within the H2a coding region permits efficient cytoplasmic accumulation of the globin cDNA transcripts. It is also shown herein that this sequence appears to suppress splicing and can functionally replace Rev and the Rev-responsive element (RRE) in the cytoplasmic accumulation of unspliced HIV-1-related mRNAs. Like RRE, this sequence acts in an orientation-dependent manner.

These results indicate that the sequence described herein, which is interchangeably referred to as a "genetic element", is a member of the class of cis-acting elements which facilitate the cytoplasmic accumulation of naturally intronless gene transcripts.

Several advantages of this invention can be appreciated. The genetic element described herein consistently and reproducibly affects an increase in mRNA levels, as well as cytoplasmic accumulation of unspliced mRNA. The described genetic element is the first cellular, non-viral element shown to be capable of achieving these results, and it is fairly well conserved throughout the animal kingdom. The genetic element of this invention allows gene expression in the absence of an intron, and simplifies the construction of cDNA expression vectors. It appears to suppress cryptic splicing events. Moreover, the histone gene from which the element is derived is abundantly expressed in essentially every mammalian cell. Thus, the described element avoids the limitations which other transport elements suffer from, e.g., limited host range or requirement for additional viral protein for activity.

The invention pertains to an isolated cis-acting cellular or non-viral genetic element (nucleic acid sequence) which suppresses splicing, enhances 3' end formation, and facilitates transport of partially spliced, alternatively spliced or fully unspliced RNA from a cell nucleus to the cytoplasm of the cell. In a particular embodiment, the nucleic acid sequence is from a histone gene, and in another embodiment the nucleic acid sequence comprises the DNA sequence of SEQ ID NO: 1. In a specific embodiment the histone gene is the H2a gene. The RNA which is transported from the nucleus to the cytoplasm can be partially spliced, alternatively spliced or fully unspliced.

The invention also relates to DNA constructs comprising the nucleic acid molecules described herein operably linked to a regulatory sequence, and to recombinant host cells, such as bacterial cells, fungal cells, plant cells, insect cells and mammalian cells, comprising the nucleic acid molecules described above operably linked to a regulatory sequence.

The invention further pertains to a method of preparing a polypeptide comprising culturing a recombinant host cell comprising a DNA construct comprising a regulatory sequence operably linked to an isolated cis-acting cellular or non-viral nucleic acid molecule described herein and DNA encoding the polypeptide to be expressed.

The invention also pertains to a method of increasing expression of a gene product from an expression vector, comprising the steps of providing a host cell containing an expression vector comprising the cis-acting genetic element described herein, DNA encoding the gene product to be expressed and a suitable promoter, and maintaining the host cell under conditions suitable for expression of the gene product. Expression of the gene product is increased relative to expression from an expression vector lacking the genetic element.

BRIEF DESCRIPTION OF THE DRAWINGS

FIGS. 3A and 3B illustrate the structures of the plasmid constructs and the demonstration that a small element in the H2a coding region is sufficient to promote the cytoplasmic accumulation of the globin cDNA transcripts. FIG. 3A shows on top the relative positions of the 101-base pair (B) and 75-base pair (N) fragments within the H2a gene. The numbers above or below indicate nucleotides relative to the transcription initiation site. Shown at the bottom are the three histone-globin chimeric gene constructs. The inserted fragments are indicated by thick lines, with the arrows depicting their orientations. Other symbols are the same as described in the description of FIG. 1. FIG. 3B is a photograph of results from RNAse protection assays of RNAs prepared from cells transfected with the indicated plasmids. "rel. cyt. accum." indicates relative cytoplasmic globin mRNA accumulation; "C/N ratio" indicates the cytoplasmic and nuclear distribution ratio.

DETAILED DESCRIPTION OF THE INVENTION

Figure 6:
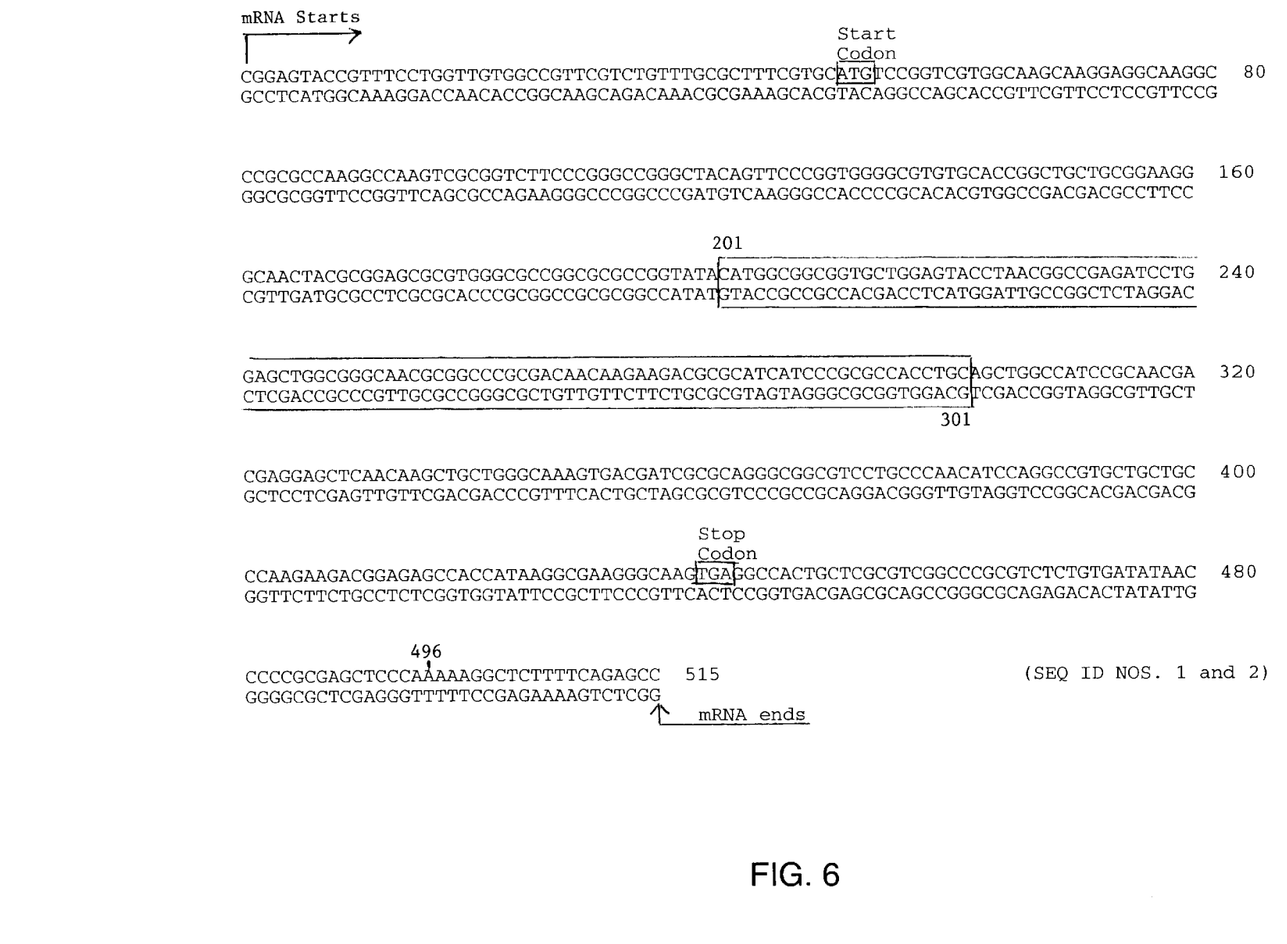
FIG. 6 is the nucleotide sequence of the mouse histone H2a gene SEQ ID NOS: 1–2. Fragment B is boxed (nucleotides 201–301).

The histone proteins are among the most abundant cellular proteins and are essential for cell viability (Kedes, Annu. Rev. Biochem. 48:837–870 (1979); Hentschel & Birnstiel, Cell 25:301–313 (1981)). Most histone mRNAs are not polyadenylated; instead, they end in highly conserved stem-loop structures (Marzluff, Gene Expression 2:93–97 (1992)). However, there are histone genes that produce polyadenylated histone mRNAs (Cheng et al., Proc. Natl. Acad. Sci. USA 86:7002–7006 (1989)), and some that usually end in the histone stem-loop can, under some circumstances, also be processed by polyadenylation (Challoner et al., Mol. Cell. Biol. 9:902–913 (1989); Kirsch et al., Genes Dev. 3:2172–2179 (1989); Mannironi et al., Nucleic Acids Res. 17:9133–9126 (1989)). Since histone mRNAs are able to efficiently accumulate in the cytoplasm without being spliced (Hentschel & Birnstiel, Cell 25:301–313 (1981)), the question of whether there are cis-acting sequences within histone genes that allow them to do so was addressed by using the mouse histone H2a gene (FIG. 6). A 101-base pair sequence within the H2a coding region was found to activate the cytoplasmic accumulation of a human β-globin cDNA transcript. It is also demonstrated herein that this sequence can functionally mimic Rev and RRE for the cytoplasmic accumulation of unspliced HIV-1-related mRNA. Thus it appears that this sequence belongs to a class of cis-acting elements that enable efficient cytoplasmic accumulation of naturally intronless gene transcripts.

Described herein is a 101-base pair cis-acting sequence contained within the mouse histone H2a gene that allows efficient cytoplasmic accumulation of intronless, differentially spliced, alternatively spliced, incompletely spliced or unspliced gene transcripts. Work described herein has (a) localized this novel cellular sequence to nucleotides 201–301 within the H2a coding region (SEQ ID NO: 1), (b) demonstrated that this sequence facilitates cytoplasmic accumulation of human β-globin cDNA transcripts, (c) provided evidence that this sequence appears to be functionally equivalent to the RRE in promoting cytoplasmic accumulation of unspliced HIV-1-related mRNA, and (d) shown that this sequence functions in an orientation-dependent manner. As used herein, "orientation-dependent" is intended to mean that activity is dependent upon the 3'/5' orientation of the sequence.

Increased cytoplasmic accumulation of mRNAs often results from enhanced nucleocytoplasmic transport. The finding described herein that the 101-base pair histone sequence permits efficient cytoplasmic accumulation of unspliced mRNAs suggests that this sequence might function as a cis-acting RNA transport element. This finding also supports the view that naturally intronless transcripts may contain positive cis-acting RNA transport elements. Importantly, the sequence identified here is the first well-characterized example of a cellular or non-viral sequence that has such a function. Sequences with a similar function have been described in two viral systems (Liu & Mertz, *Genes Dev.* 9:1766–1780 (1995); Huang & Liang, *Mol. Cell. Biol.* 13:7476–86 (1993); Huang & Yen, *Mol. Cell. Biol.* 15:3864–3869 (1995)). It has been recently reported that an RNA sequence (called the posttranscriptional regulatory element, or, PRE) located at the 3' region of intronless HBV transcripts promotes efficient cytoplasmic accumulation of the viral mRNAs (Huang & Liang, *Mol. Cell. Biol.* 13:7476 86 (1993); Huang & Yen, *Mol. Cell. Biol.* 15:3864–3869 (1995)). Similarly, a cis-acting sequence (called the post-transcriptional processing element, or PPE) present in the coding region of the HSV-TK transcript has been shown to have the same effects (Liu & Mertz, *Genes Dev.* 9:1766–1780 (1995)). Like the histone sequence, both viral elements can functionally replace introns for the expression of intron-dependent genes and appear to rely on cellular factors for their function. It is thus highly likely that it may be a general situation for other intronless genes to contain positive cis-acting transport elements that facilitate their nuclear export.

The precise mechanism by which the histone sequence facilitates cytoplasmic accumulation of intronless gene transcripts is not yet known. One hypothesis is that this sequence might function by directly promoting histone mRNA nuclear export. As shown in this study, the histone sequence acts constitutively to transport unspliced HIV-1-related mRNA to the cytoplasm in the absence of Rev. Additionally, it appears to have an inhibitory effect on splicing. Further, these functions are orientation-dependent. Furthermore, for maximal effect it is preferable that the element be located within the transcript to be expressed, e.g., within the open reading frame, within an intron, or within the 3'- or 5'-untranslated region.

As Rev/RRE also has been reported to inhibit splicing as well as promote RNA transport, the histone sequence functionally mimics Rev/RRE. Accumulated data have suggested that Rev may facilitate the nuclear export of unspliced HIV-1 mRNA by directly interacting with the cellular export machinery (Malim & Cullen, *Mol. Cell. Biol.* 13:6180–6189 (1993); Bogerd et al., *Cell* 82:485–494 (1995); Fischer et al., *Cell* 82:475–483 (1995); Fritz et al., *Nature* 376:530–533 (1995); Kalland et al., *Mol. Cell. Biol.* 14:7436–7444 (1994); Malim et al., *Cell* 58:205–214 (1989); Meyer & Malim, *Genes Dev.* 8:1538–1547 (1994); Pfeifer et al., *Eur. J. Biochem.* 199:53–64 (1991); Stutz et al., *Cell* 82:495–506 (1995)). It is thus plausible that the histone sequence might function by a similar mechanism, i.e., by interacting with a cellular factor(s) whose function is analogous to that of Rev.

3' end processing has been shown to play an essential role in the mRNA nuclear export. Studies have indicated that polyadenylation promotes mRNA transport from the nucleus to the cytoplasm (Huang & Carmichael, *Mol. Cell. Biol.* 16:1534–1542 (1996); Eckner et al., *EMBO J.* 10:3513–3522 (1991)). Likewise, histone 3' end processing has been implicated in the nuclear export of histone mRNAs (Eckner et al., *EMBO J.* 10:3513–3522 (1991); Williams et al., *Nucleic Acids Res* 22:4660–4666 (1994)). Thus, the formation of a mature 3' end, either by polyadenylation or by the histone processing machinery, might direct the messages along a pathway that leads to the nuclear pore. Evidence exists that the presence of introns can activate polyadenylation (Nesic et al., *Mol. Cell. Biol.* 13:3359–3369 (1993); Collis et al., *EMBO J.* 9:233–240 (1990); Huang & Gorman, *Nucleic Acids Res.* 18:937–947 (1990); Liu & Mertz, *Nucleic Acids Res* 21:5256–63 (1993); Liu & Mertz, *Nucleic Acids Res.* 24:1765–1774 (1996); Niwa et al., *Genes Dev.* 4:1552–1559 (1990); Pandey et al., *Nucleic Acids Res* 18:3161–70 (1990)). These data indicate that part of the function of the histone sequence might mimic introns that act to enhance polyadenylation, as recent results also suggest that the histone sequence facilitates polyadenylation, which in turn might lead to efficient RNA nuclear export.

Inhibition of splicing by the histone sequence suggests that it might be a natural function of this sequence to block potential spliceosome formation on histone mRNAs. This might be a general aspect of transport elements for intronless gene transcripts, as these transcripts may contain cryptic or non-consensus splice sites. Without wishing to be bound by theory, it appears that the described histone element binds a cellular protein(s), inhibits the process of splicing, and enhances the process of polyadenylation.

The identification of the histone sequence suggests that transcripts can have more than one positive element that signal nuclear export. In the case of the H2a mRNA, these positive elements include the sequence identified in this work, sequences involved in 3' end processing, and perhaps, the 5' cap structure as well (Dargemont & Kühn, *J. Cell Biol.* 118:1–9 (1992); Hamm & Mattaj, *Cell* 63:109–118 (1990); Izaurralde et al., *J. Cell Biol.* 118:1287–1295 (1992)). These elements may act in concert to allow for efficient nucleo-cytoplasmic transport of H2a mRNA. Although the histone 101-base pair sequence is sufficient to activate the cytoplasmic accumulation of the intronless gene transcripts, it does not appear to be fully functional compared to the 498-base pair gene product. Therefore, the H2a coding region might contain more than one such sequence.

An interesting aspect of this study is that the histone sequence defined herein overlaps with the histone promoter enhancer region (Bowman & Hurt, *Nucleic Acids Res.* 23:3083–3092 (1995); Hurt et al., *Proc. Natl. Acad. Sci. USA* 86:4450–4454 (1989); Hurt et al., *Mol. Cell. Biol.* 11:2929–2936 (1991); Kalukov et al., *Nucleic Acids Res.* 24:523–531 (1996)). However, the sequence used does not display significant transcription enhancement activity, perhaps due to the different promoters used and the different experimental context. Additionally, when the entire H2a transcribed region was inserted upstream of the promoter region in some of the constructs, it did not behave as a promoter. Nevertheless, it remains possible that this histone sequence can function both at the DNA (for transcription enhancement) and RNA levels (for mRNA export).

It has been well established that the histone 3' end processing (not polyadenylation) and the histone promoters are the targets for the cell cycle regulation (Harris et al., *Mol Cell Biol* 11:2416–24 (1991); Sittman et al., *Proc Natl Acad Sci USA* 80:1849–53 (1983)). Replacement of the histone 3' processing sequences with polyadenylation signals led to cell cycle-independent histone expression (Cheng et al., *Proc. Natl. Acad. Sci. USA* 86:7002–7006 (1989);Kirsch et al., *Genes Dev.* 3:2172–2179 (1989); Levine et al., *Proc Natl Acad Sci USA* 84:6189–93 (1987)). Based on these data, it appears that the function of the histone sequence (in mRNA transport) is probably not cell cycle-regulated.

In summary, a novel cellular (or non-viral) sequence in the mouse histone H2a gene has been identified that appears to function constitutively to facilitate the cytoplasmic accumulation of intronless gene transcripts. This sequence can also functionally mimic the Rev/RRE system in an HIV-1-based construct: it can replace Rev and RRE for the efficient cytoplasmic accumulation of unspliced HIV-1-related mRNA, and it appears to suppress splicing. Moreover, it is found in the rather abundant and ubiquitous messages for histone H2a, and is thus not likely to be cell-type or species-dependent in its action. This suggests that all histone messages have a similar element and suggests that the natural abundance of these messages should make it possible to identify and isolate the factor(s) involved. As such, it is of interest not only in furthering understanding of mRNA transport, but also in applications such as the expression of cDNAs using recombinant vectors, or as an aid in gene therapy.

Accordingly, the invention provides an isolated cis-acting cellular or non-viral nucleic acid molecule which suppresses splicing and facilitates transport of partially spliced, alternatively spliced or fully unspliced RNA from a cell nucleus to the cytoplasm of the cell. As appropriate, nucleic acid molecules of the present invention can be RNA, for example, mRNA, or DNA, such as cDNA and genomic DNA. DNA molecules can be double-stranded or single-stranded; single-stranded RNA or DNA can be either the coding, or sense, strand or the non-coding, or antisense, strand. Preferably, the nucleic acid molecule comprises at least about 75 nucleotides, more preferably at least about 101 nucleotides, and even more preferably at least about 400 nucleotides. The nucleotide sequence can be only that which encodes at least a fragment of the histone gene product. Additionally, the nucleotide sequence can be fused to a marker sequence, for example, a sequence which encodes a polypeptide to assist in isolation or purification of the nucleic acid molecule. Such sequences include, but are not limited to, those which encode a glutathione-S-transferase (GST) fusion protein and those which encode a hemaglutin A (HA) peptide marker from influenza.

As used herein, an "isolated" gene or nucleic acid molecule is intended to mean a gene or nucleic acid molecule which is not flanked by nucleotide sequences which normally (in nature) flank the gene or nucleic acid sequence (as in genomic sequences) and/or has been completely or partially purified from other transcribed sequences (as in a cDNA or RNA library). Thus, an isolated gene or nucleic acid molecule can include a gene or nucleotide sequence which is synthesized chemically or by recombinant means. Thus, recombinant DNA contained in a vector are included in the definition of "isolated" as used herein. Also, isolated nucleotide sequences include recombinant DNA molecules in heterologous host cells, as well as partially or substantially purified DNA molecules in solution. In vivo and in vitro RNA transcripts of the DNA molecules of the present invention are also encompassed by "isolated" nucleotide sequences. Such isolated nucleotide sequences are useful as probes for isolating homologous sequences (e.g., from other mammalian species), for gene mapping (e.g., by in situ hybridization with chromosomes), or for detecting expression of the histone gene in tissue (e.g., human tissue), such as by Northern blot analysis.

The invention also encompasses variations of the nucleic acid molecules of the invention, such as those encoding portions, analogues or derivatives of the genetic element. Such variations can be naturally-occurring, such as in the case of allelic variation, or non-naturally-occurring, such as those induced by various mutagens and mutagenic processes. Included variations include, but are not limited to, addition, deletion and substitution of one or more nucleotides. Preferably, the nucleotide alterations are silent; that is, they do not alter the characteristics or activity of the genetic element.

The invention described herein also relates to portions of the isolated nucleic acid molecules described herein which retain the ability to suppress splicing and facilitate transport of partially spliced, alternatively spliced or fully unspliced RNA from the nucleus to the cytoplasm. The term "fragment" is intended to encompass a portion of a nucleotide sequence described herein which is from at least about 25 contiguous nucleotides to at least about 50 contiguous nucleotides or longer in length; such fragments are useful as probes, e.g., for in situ hybridization, and also as primers. Particularly preferred primers and probes selectively hybridize to the nucleic acid molecule encoding the genetic element described herein.

The invention also pertains to nucleotide sequences which hybridize under medium stringency hybridization conditions (e.g., for selective hybridization) to a portion of a nucleotide sequence described herein. Appropriate stringency conditions are known to those skilled in the art or can be found in standard texts such as *Current Protocols in Molecular Biology*, John Wiley & Sons, N.Y. (1989), 6.3.1–6.3.6. Such hybridizable nucleotide sequences are useful as probes and primers for diagnostic applications.

Accordingly, the invention pertains to nucleotide sequences which have a substantial identity with the nucleotide sequences described herein; particularly preferred are nucleotide sequences which have at least about 80%, and more preferably at least about 90% identity with nucleotide sequences described herein. For example, preferred nucleotide sequences encoding a genetic element having the same or similar biological activity as the novel genetic element described herein are within the scope of the invention. Moreover, nucleotide sequences which have lower levels of identity but which share similar secondary structure (as determined, for example, as described in Gorodkin et al., Nucleic Acids Res. 18:3724–3732 (1997)) and which have the same or similar biological activity as the genetic element described herein are within the scope of the invention. As used herein, activities of the genetic element include, but are not limited to, suppression of splicing and facilitation of transport of partially spliced, alternatively spliced or fully unspliced RNA from nucleus to cytoplasm.

The invention also provides expression vectors containing an isolated cis-acting cellular or non-viral nucleic acid sequence described herein operably linked to at least one regulatory sequence. Many suitable vectors are commercially available into which the described cis-acting element can be incorporated, and other suitable vectors can be readily prepared by the skilled artisan. "Operably linked" is intended to mean that the nucleotide sequence is linked to a regulatory sequence in a manner which allows expression of the nucleic acid sequence; the regulatory sequence need not be directly linked to the cis-acting nucleic acid sequence. Regulatory sequences are art-recognized, and the term "regulatory sequence" includes promoters, enhancers, and other expression control elements which are described in Goeddel, *Gene Expression Technology: Methods in Enzymology* 185, Academic Press, San Diego, Calif. (1990). For example, regulatory sequences native to the transformed host cell can be employed. It should be understood that the design of the expression vector may depend on such factors as the choice of the host cell to be transformed and/or the type of gene product desired to be expressed. For instance, polypeptides can be produced by ligating the cloned gene, or a portion thereof, into a vector suitable for expression in either prokaryotic cells, eukaryotic cells or both (see, for example, Broach, et al., *Experimental Manipulation of Gene Expression*, ed. M. Inouye (Academic Press, 1983) p. 83; *Molecular Cloning: A Laboratory Manual,* 2nd Ed., ed. Sambrook et al. (Cold Spring Harbor Laboratory Press, 1989) Chapters 16 and 17), along with appropriate regulatory sequences and the cis-acting genetic element of the present invention. Typically, expression constructs will contain one or more selectable markers, including, but not limited to, the gene that encodes dihydrofolate reductase and the genes that confer resistance to neomycin, tetracycline, ampicillin, chloramphenicol, kanamycin and streptomycin resistance. Suitable expression vectors include, but are not limited to, the expression vectors described herein in the Examples.

Prokaryotic and eukaryotic host cells transfected by the described vectors are also provided by this invention. For instance, cells which can be transfected with the vectors of the present invention include, but are not limited to, bacterial cells such as *E. coli* (e.g., *E. coli* K12 strains), Streptomyces, Pseudomonas, *Serratia marcescens* and *Salmonella typhimurium*, insect cells (baculovirus), including Drosophila, fungal cells, such as yeast cells, plant cells and mammalian cells, such as thymocytes, Chinese hamster ovary cells (CHO), and COS cells e.g., COS7 cells.

Thus, a cis-acting cellular or non-viral nucleic acid molecule described herein can be used to produce a recombinant form of a protein or polypeptide via microbial or eukaryotic cellular processes. Ligating the cis-acting cellular nucleic acid molecule into a gene construct, such as an expression vector, along with DNA encoding the gene product (e.g., protein, polypeptide or nucleic acid) to be expressed and a suitable regulatory sequence, and transforming or transfecting into hosts, either eukaryotic (yeast, avian, insect, plant or mammalian) or prokaryotic (bacterial cells), are standard technical procedures used in producing many proteins. Similar procedures, or modifications thereof, can be employed to prepare recombinant proteins as described herein by microbial means or tissue-culture technology. Accordingly, the invention pertains to the production of proteins or polypeptides by recombinant technology utilizing the cis-acting cellular nucleic acid molecule described herein.

Proteins and polypeptides produced by these methods can be isolated or purified (e.g., to homogeneity) from recombinant cell culture by a variety of processes. These include, but are not limited to, anion or cation exchange chromatography, ethanol precipitation, affinity chromatography and high performance liquid chromatography (HPLC). The particular method used will depend upon the properties of the polypeptide and the selection of the host cell; appropriate methods will be readily apparent to those skilled in the art.

The present invention also pertains to pharmaceutical compositions comprising compositions (e.g., nucleic acid molecules, DNA constructs) described herein. For instance, a composition of the present invention can be formulated with a physiologically acceptable medium to prepare a pharmaceutical composition. The particular physiological medium may include, but is not limited to, water, buffered saline, polyols (e.g., glycerol, propylene glycol, liquid polyethylene glycol) and dextrose solutions. The optimum concentration of the active ingredient(s) in the chosen medium can be determined empirically, according to well known procedures, and will depend on the ultimate pharmaceutical formulation desired. Methods of introduction of exogenous compounds at the site of treatment include, but are not limited to, intradermal, intramuscular, intraperitoneal, intravenous, subcutaneous, oral and intranasal. Other suitable methods of introduction can also include gene therapy, rechargeable or biodegradable devices and slow release polymeric devices. The pharmaceutical compositions of this invention can also be administered as part of a combinatorial therapy with other agents. For example, the described cellular or non-viral cis-acting genetic element can be used to replace Rev/REE in HIV for used as a gene therapy vehicle or vaccine (Temin, *PNAS* 90:4419 (1993)).

The described element can be used to enhance expression from intronless constructs, e.g., cDNA constructs, in either cultured cells (introduced by transfection or by viral vectors) or in animals (e.g., by transgenic technology). The element described herein can also be useful in gene therapy applications, where cDNA constructs are often used for expression in vivo; the element of this invention can be used to replace the currently used system of recombinant retrovirus vectors. The described histone element can also be used in antisense RNA applications, where antisense RNA is used as a means to inhibit target gene expression. The element leads to enhanced Levels of antisense, thereby improving efficacy.

The histone H2a open reading frame can also be examined to identify redundant or independent elements which function in the transport process. For example, it can be determined whether the element is necessary for H2a mRNA transport by deleting the 101-base pair sequence from the H-βG construct and determining whether this deletion abolishes the ability of the histone sequences to enhance cytoplasmic RNA levels. The histone H2a element described herein can also be used to screen other mammalian histone open reading frames for sequences that facilitate intronless mRNA transport, utilizing the same methods applied to histone H2a. The histone H2a gene is part of a gene cluster with the histone H3.2 gene; thus, the H3.2 open reading frame, for example, can be analyzed for transport elements, along with the H4 gene. As naturally-polyadenylated histone mRNAs accumulate in the cytoplasm efficiently, they will also be valuable sources to look at in future experiments. These studies will provide insights into common elements that allow histone mRNA transport as well as information useful in predicting consensus sequences and/or important RNA secondary structures.

Thus, the invention provides a method of preparing a polypeptide comprising culturing a recombinant host cell comprising a DNA construct comprising a regulatory sequence operably linked to an isolated cis-acting cellular or non-viral nucleic acid molecule described herein and DNA encoding the polypeptide to be expressed. The invention also provides a method of increasing expression of a gene product from an expression vector, comprising the steps of providing a host cell containing an expression vector comprising a regulatory sequence operably linked to the cis-acting cellular or non-viral nucleic acid molecule described herein and DNA encoding the gene product to be expressed, and maintaining the host cell under conditions suitable for expression of the gene product, whereby expression of the gene product is increased relative to expression from an expression vector lacking the cis-acting cellular nucleic acid molecule.

The invention also comprises a method of suppressing splicing, enhancing 3' end formation and/or facilitating transport to the cytoplasm of a gene transcript, comprising incorporating in the transcript a cis-acting cellular nucleic acid molecule which suppresses splicing, enhances 3' end formation and/or facilitates transport of RNA from a cell nucleus to the cytoplasm of the cell. The incorporation of the cis-acting cellular nucleic acid molecule into the transcript will typically take place at the DNA level.

The processes described herein can also be used to further define the minimal requirements for a functional element. Constructs similar to those described herein can be made which include progressive 5' and 3' deletions from the edges of the histone H2a open reading frame and of the 101-base pair element. To further define minimal requirements, internal mutations can be made using the technique of linker scanning (Sambrook et al., *Molecular Cloning, A Laboratory Manual,* 2nd edition, sections 15.32–15.50 (1989)). Once a truly minimal element is defined, point mutations can be introduced at positions suspected to be important due to base-pairing interactions in putative secondary structures, or due to strong conservation between different histone H2a genes.

Once the most effective minimal element(s) is identified, the trans-acting factor(s) responsible for the effects can be identified as follows:

a. Gel Shift Assays

Once a minimal RNA element is defined by the experiments outlined above, in vitro transcription with phage T7 or T3 RNA polymerase can be used to produce $^{32}$P-labeled transcripts. These are mixed with HeLa cell nuclear extracts prepared by the procedure of Dignam (*Nucleic Acids Res.* 11:1475–1489 (1983)). Electrophoresis can then be used to resolve unbound and bound RNA molecules. tRNA can serve as a general non-specific inhibitor of protein-RNA interactions, but a number of other RNAs can be used to examine the specificity of observed interactions. These include transcripts of the human β-globin cDNA, transcripts of fragments from within the H2a region, and transcripts of linker scanning mutant fragments of the minimal elements that do not have the activities in vivo. Results of the assay will provide useful information on the specificity of the interaction of nuclear factors with the element. If shifts are not observed in initial experiments, variations can be tried, including, altering salt, magnesium and pH, fractionating the extracts over heparin-agarose and/or by ammonium sulfate precipitation, and covalently crosslinking the substrate and protein before electrophoresis.

b. UV-Crosslinking

This technique offers the potential to reveal the molecular weight of polypeptides that interact directly with DNA or RNA molecules. In vitro labeled minimal element fragment are incubated with HeLa cell nuclear extracts in the presence of excess amounts of appropriate unlabeled competitor RNAs, and subjected to UV-crosslinking with shortwave UV using a Stratalinker from Stratagene. Then, cross-linked products will be treated with RNAses A and T1, and subjected to SDS-PAGE along with molecular weight standards. The molecular weights of the bound proteins will be compared with those of known hnRNPs. If it appears that a known hnRNP protein might interact with the histone element, then antibodies to the hnRNP protein(s) can be obtained and used in supershift assays (if they bind to the protein interacting with the histone element, then they would retard, or "supershift" the shifted band in the gel shift assay). If this is the case, it means that a known nuclear RNA-binding protein might be involved in the transport of a specific, abundant cellular message. In this way, Liu and Mertz (*Genes Dev.* 9:1766–1780 (1995)) identified hnRNP L as a possible transport protein for the HSV1-TK message.

c. Purification of the Protein

Standard methods can be used to purify the proteins that interact with the element. These include ammonium sulfate fractionation, DEAE-Sephadex chromatography and use of a FPLC machine. HeLa cell nuclear extracts will be used for the protein source and gel shifts will be the assay. If the gel shift assays do not work, then UV-crosslinking can be used as an assay for protein purification. As described above, competition assays can also be performed. It is also possible to use affinity chromatography using tandem repeats to purify the protein, although this will be difficult because of the difficulty in preparation of large amounts of specific RNA for coupling to CNBr-activated Sepharose.

d. Northwestern Plots of a Mouse cDNA Expression Library

A mouse NIH3T3 cDNA expression library has been constructed in the phage 1ZAPII expression system. This library has been screened with tandem repeats of a DNA element; this same library can be used to screen for factors that specifically interact with a function histone H2a transport element. The specific methods used have been described by Qian and Wilusz for the purification of a polypyrimidine-rich element-binding factor (*Analyt. Biochem.* 212:547–554 (1993)).

e. Yeast Three-hybrid System

The yeast three-hybrid system has proven a useful technique in purifying several RNA-binding proteins (SenGupta et al., *PNAS* 93:8496–8501 (1996)). This technique is similar in logic to the much used yeast two-hybrid system, but relies on protein-RNA interactions to tether an enhancer-binding protein to a transcription activating protein. The three-hybrid system can be used in the identification of proteins that interact specifically and tightly with the histone H2a transport element. Importantly, Wang et al. have recently used this technique to successfully clone the cDNA for the protein, SLBP, that specifically binds to the histone 3'-end stem-loop (*Genes Dev.* 10:3028–3040 (1996)). The minimal element sequence or tandem repeats (which have been shown in other work to function better than the single) can be used as a bait in the screen. As this system is believed to yield some number of artifactual clones, great care must be given to verifying that any positive clones are analyzed for expression of factors specific for functional sequences identified.

Identification of a putative protein can be followed by additional work, including cloning of the cDNA for this factor, overexpressing in any of a number of available systems (e.g., DNAs using GST-fusion and His-tag vectors in *E. coli*, and in baculovirus constructs in insect cells), obtaining antibodies and performing in vitro studies with functional and nonfunctional sequences. If in vivo studies indicate that the three effects (e.g., enhancement of transport, inhibition of splicing and 3'-end processing), co-reside within the minimal element, in vitro analysis can be performed to gain a better understanding on how the factor works. Antibodies to a factor can be used in immunoprecipitation studies to determine whether there might also be other polypeptides involved that were missed in the above-described work. If other polypeptides are involved, they will be pursued as well.

a. Role in Inhibiting Splicing

Results presented above indicate that the described histone element and the HIV1 Rev/RRE system appear to share the ability to suppress the process of pre-mRNA splicing. It may be useful to known at which step the element/protein blocks splicing. For this work a well-characterized in vitro splicing system used to shed light on the mechanism of Rev function can be used (Kjems et al., Cell 67:169–178 (1991); Kjems and Sharp, J. Virol 67:4769–4776 (1993)). To analyze effects of the element/protein on splicing, the element can be inserted into the intron region of rabbit β-globin pre-mRNA or a modified version of the adenovirus major late transcript. The efficiency of splicing and spliceosome formation can be compared between pre-mRNAs containing or lacking the insert, as well as in the presence or absence of any purified protein (immunodepletion of the protein from the splicing mix).

b. Role in 3'-end Processing

The histone H2a open reading frame appears to have the capacity to enhance 3'-end formation when inserted into the human β-globin cDNA. If this property is retained in the minimal element defined for transport, in vitro experiments can be undertaken to determine whether the element (or factor that interacts with it) has any effect on pre-mRNA cleavage/polyadenylation. Enhanced cleavage/polyadenylation of the substrate with the insertion of the element compared to that without the insertion indicates a positive role of this element in 3'-end processing.

From results described herein, the 101-base pair histone element mimics the HIV1 Rev/RRE, the HBV element and the HSV-TK element in many of their effects. It is possible that a general feature of mRNA "transport elements" is not only transport, but also the entire collection of observed phenotypes, which include splicing inhibition, possible 3'-end processing enhancement and transport. These processes may be closely interconnected in the nucleus, and the distinction between them and factors which interact with them may be ambiguous. To this end, further analysis can be carried out, both in vivo and in vitro, relating to the effects of each of these sequences on both splicing and polyadenylation. Results of the experiments will provide insights into whether RNA processing and transport are generally coupled and whether the histone cellular element works in a similar way to Rev/RRE and the other viral elements.

EXAMPLES

Material and Methods

Constructs

Figure 1:
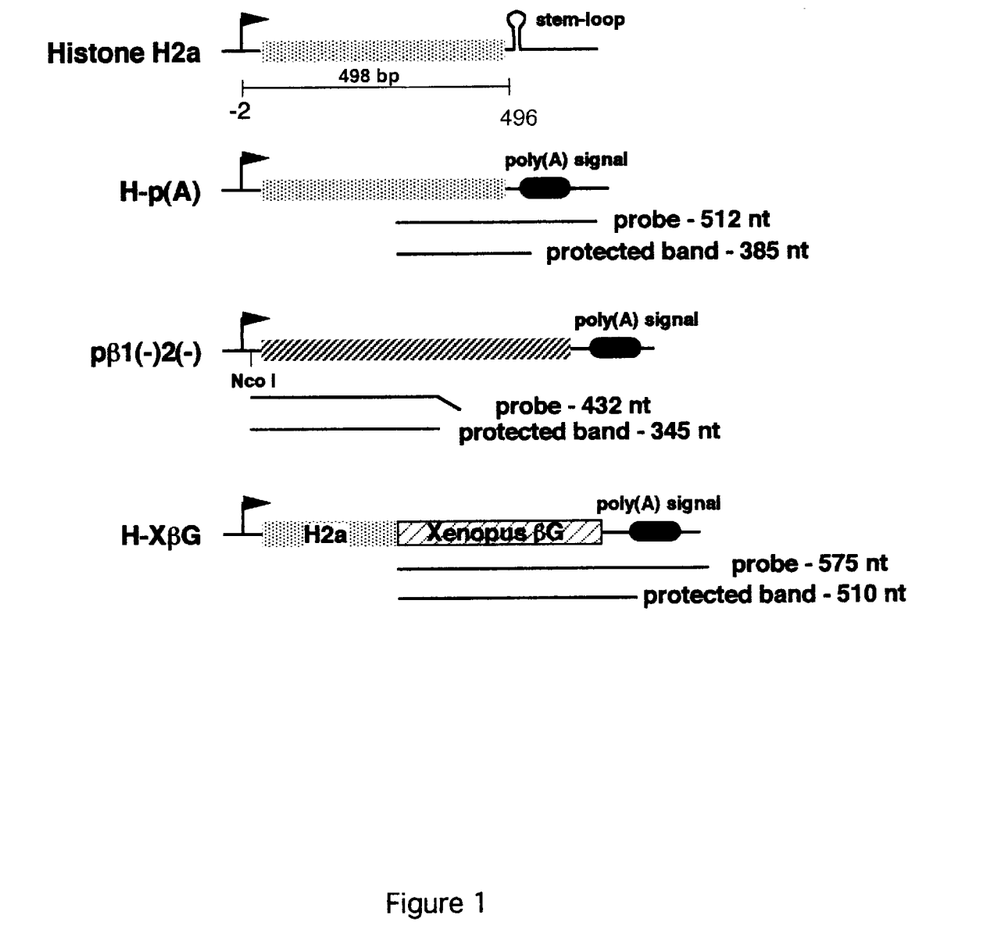
FIG. 1 is a schematic diagram of the plasmids used to construct H-p(A). The gray box represents the coding region of the H2a gene. The hatched boxes indicate either human or Xenopus β-globin genes. The arrows indicate transcriptional start sites. The thin line below the histone H2a construct marks the region used to build H-p(A). The numbers beneath the line represent nucleotides relative to the transcription start site. The probes used in RNAse protection assays and the protected bands are indicated. The tilted portions of the probes depict non-homologous sequences derived from plasmid vectors. In pβ1(-)2(-), the unique Nco I site is marked. Sizes are not to scale.
Figure 2:
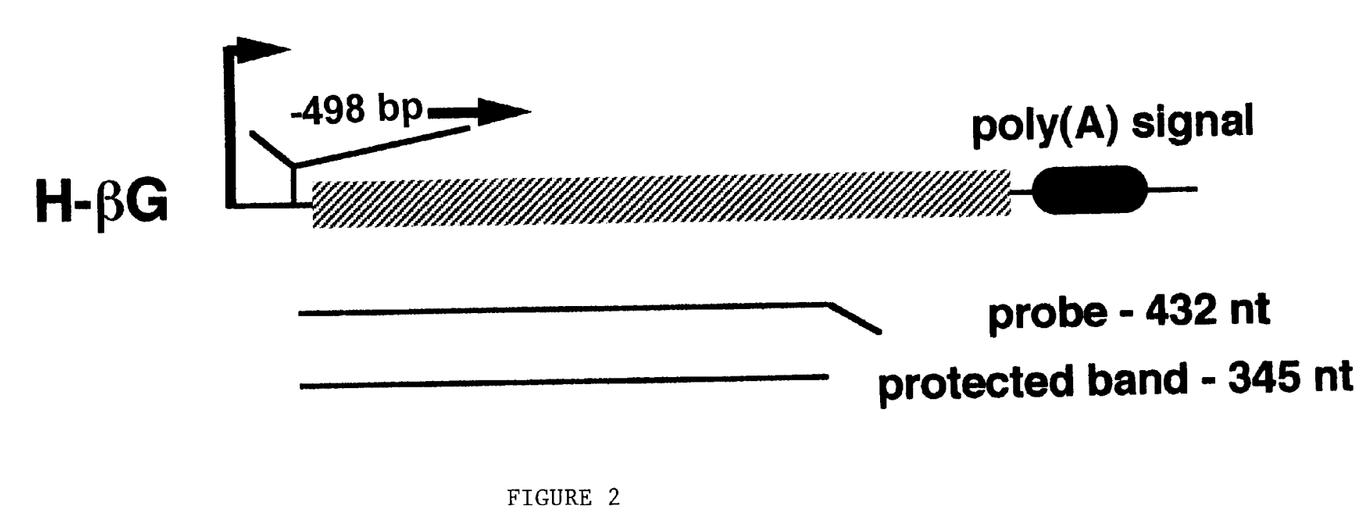
FIG. 2 illustrates the structure of construct H-βG. The 498-base pair histone fragment inserted at the unique NcoI site is shown, with its orientation indicated. Other symbols are the same as those described in the description of FIG. 1.
Figure 3A:
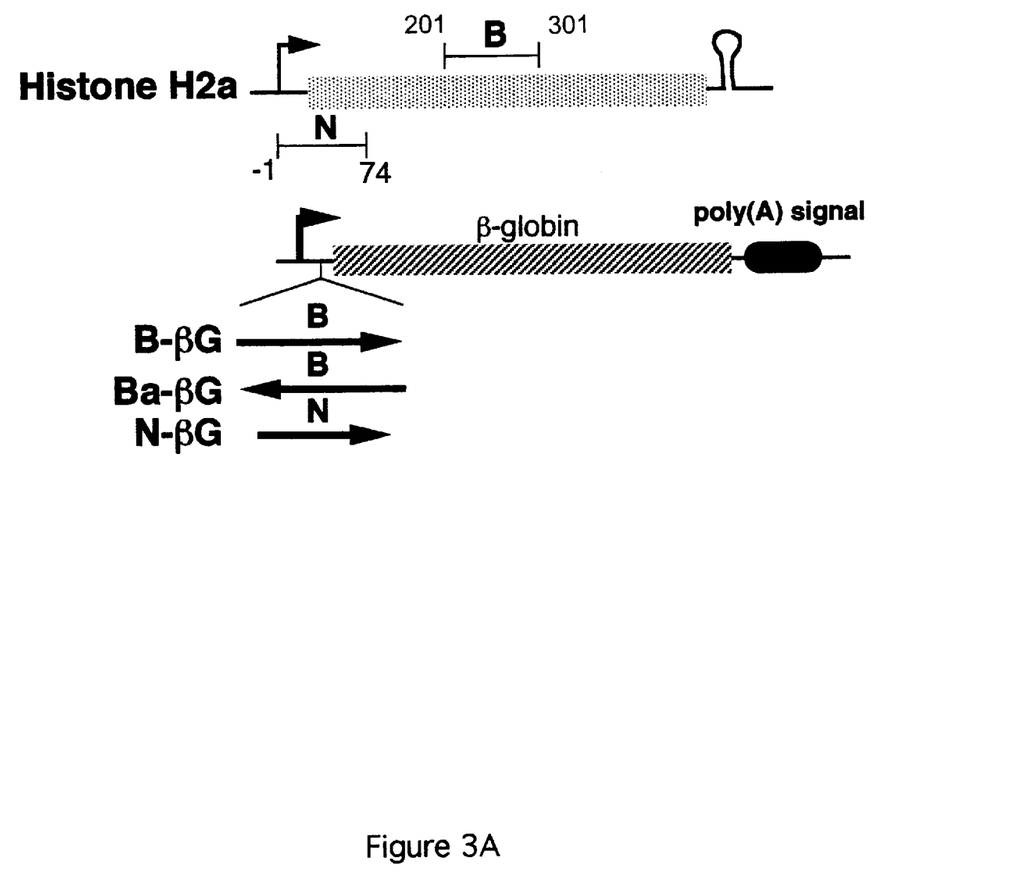
Figure 4:
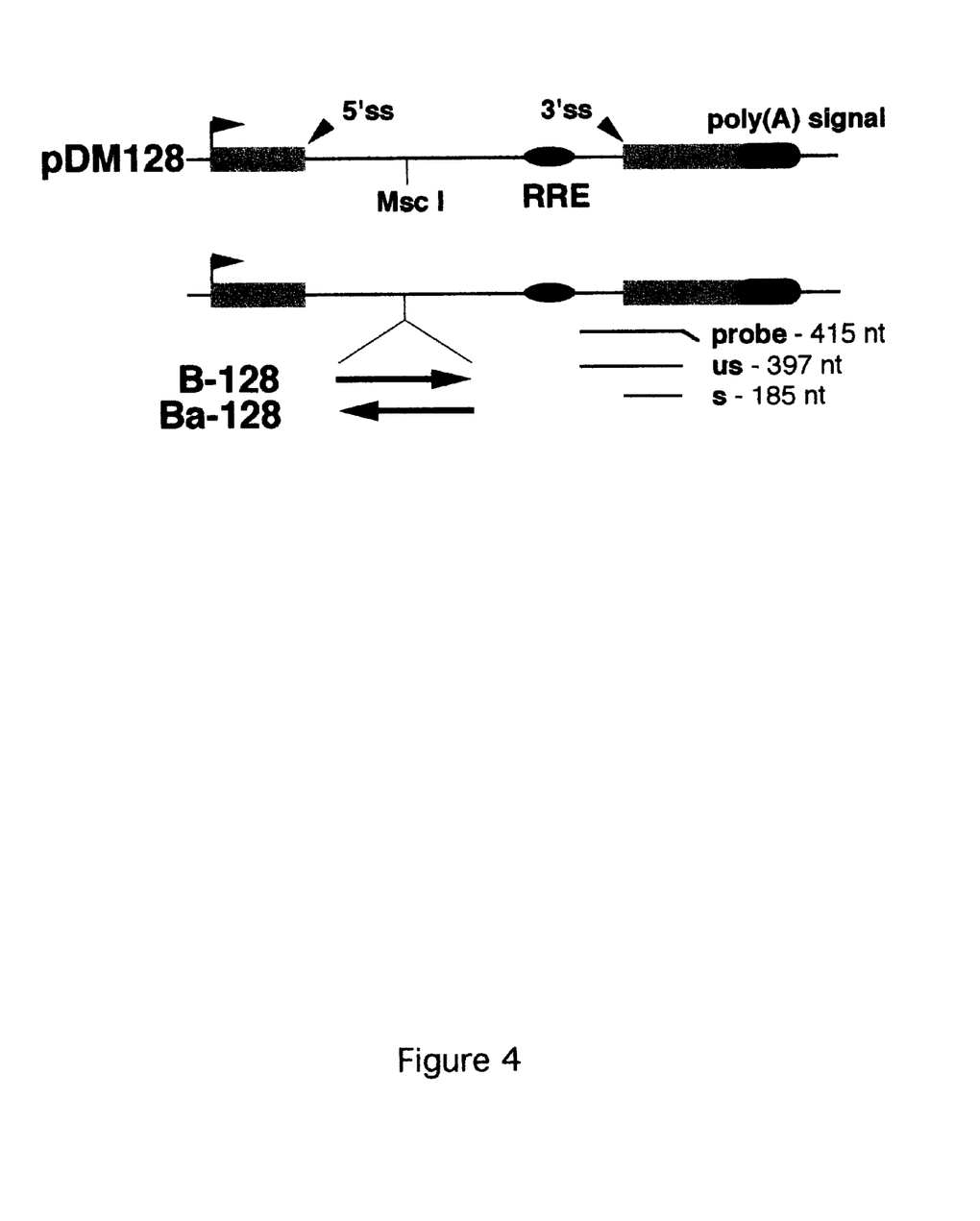
FIG. 4 illustrates the structures of the plasmid constructs used to demonstrate that the histone element functionally mimics the Rev/RRE system. The gray boxes and the thin lines denote the exon and the intron sequences from the HIV-1 gene, respectively. The RRE sequence and the unique MscI site are also marked. In B-128 and Ba-128, the inserted histone sequences are indicated, with the arrows depicting the orientations. "5' ss" indicates the 5' splice site; "3' ss" indicates the 3' splice site; "us" indicates unspliced RNA; and "s" indicates spliced RNA.

The mouse histone H2a gene-containing plasmid, MM614 (Graves et al., J. Mol. Biol. 183:179–194 (1985)), and plasmids pb1(−)2(−) (Yen, Semin. Virol. 4:33–42 (1993); Ryu & Mertz, J Virol 63:4386–94 (1989)), pDM128 and pRSV-Rev (Hope et al., Proc. Natl. Acad. Sci. USA 87:7787–7791 (1990); Peterlin et al., Proc Natl Acad Sci U.S.A. 83:9734–9738 (1986)) have been previously described. H-p(A) was created by inserting the 498-base pair H2a PCR fragment (nucleotides −2 to 496 relative to the H2a transcription start site) into a pBlueScript-based expression vector (FIG. 1). Transcription is driven by the CMV immediate early promoter, and the 3' RNA end is formed by the rabbit β-globin poly(A) signal. H-βG was constructed by cloning the 498-base pair fragment into a unique Nco I site at the globin 5' untranslated region in pb1(−)2(−) (FIG. 2). B-βG and Ba-βG were created by inserting the 101-base pair H2a PCR fragment (fragment B, nucleotides +201 to +301, relative to the transcription start site) into pβ1(−)2(−) at the Nco I site in the sense and antisense orientations, respectively (FIG. 3A). N-βG was created by cloning the 75-base pair PCR fragment (fragment N, nucleotides −1 to +74 relative to the transcription start site) into pb1(−)2(−) at the NcoI site in the sense orientation. B-128 was made by cloning fragment B into pDM128 at the unique MscI site. Ba-128 is identical to B-128 except that fragment B was inserted in the antisense orientation (FIG. 4A).

H-XβG was created by placing a *Xenopus laevis* β-globin cDNA immediately 3' of the histone sequence in H-p(A) (FIG. 1). This chimeric gene expresses messages that partition between the nucleus and the cytoplasm in a reproducible manner. This construct was used in all experiments as an internal control both for transfection efficiency and for subcellular fractionation.

Cells and Transfections

COS7 cells were maintained and propagated as previously described (Huang & Carmichael, Mol. Cell. Biol. 16:1534–1542 (1996)). Transfections were carried out with a modified CaPO$_4$ DNA co-precipitation method (Cahill & Carmichael, J. Virol. 63:3634–3642 (1989)). Approximately 6 hours prior to transfection, cells were diluted 2-fold and replated in 150 mm plates. Five µg of reporter DNA (pb1 (−)2(−), H-p(A), H-βG, B-βG, Ba-βG, N-βG, pDM128, B-128 or Ba-128), 5 µg of the control DNA H-XβG and 25 µg of pBlueScript DNA or of Rev-expressing plasmid (pRSV-Rev) were used per plate for transfection.

RNA Preparation

Nuclear and cytoplasmic RNAs were isolated 48 hours after transfection. For the preparation of cytoplasmic RNA, cells were rinsed free of media with ice-cold PBS and were then disrupted with an NP40 lysis buffer (10 mM Hepes, pH 7.6, 10 mM NaCl, 3 mM MgCl$_2$ and 0.5% NP40) on ice for 30 seconds. Cytoplasmic lysates were collected in new tubes and appropriate amounts of guanidinium thiocyanate crystals were added to give a final concentration of 4M. Cytoplasmic RNA was then purified through 5M CsCl step gradients. For nuclear RNA, the above intact cell nuclei which were still attached to the plates were rinsed with ice-cold NP40 buffer followed by lysis in 4M guanidinium isothiocyanate, 20 mM sodium acetate, pH 5.2, 0.1 mM dithiothreitol, and 0.5% N-lauryl sarcosine. The RNA was then pelleted through cesium chloride as described above.

RNAse Protection Assays

Internally labeled RNA probes were made by in vitro transcription by T3 or T7 RNA polymerase in the presence of [α-32P] UTP. DNA templates were removed by RQ1 DNase digestion followed by phenol/chloroform extraction. Internally-labeled riboprobes were hybridized to target RNAs at 60° C. overnight, as described previously (Adami et al., J. Virol. 63:85–93 (1989)). The hybridization products were digested with a T1/T2 mixture (Lichtler et al., Biotechniques 12:231–232 (1992)) at 37° C. for 1.5 hours and the resulting samples were resolved on 6% denaturing polyacrylamide gels. Routinely, 50% volume of total nuclear and cytoplasmic RNA samples were used for each RNAse protection assay.

Quantitation of RNAse Protection Data

Protected bands were quantitated using a Packard Instant Imager. Background was subtracted using regions of identical size located immediately below each of the experimental bands. When bands within the same lane were compared, values were adjusted for length and uridine content, because the radioactive probes used were internally labeled with $^{32}$P-UTP.

In order to accurately determine the subcellular distribution of various RNAs, the c/n ratio of RNA expressed from the internal control plasmid H-XβG was used to normalize all experimental results. In different experiments, this ratio varied slightly. A 0.50 was arbitrarily set as a standard ratio for normalization purposes, and values for other RNAs were adjusted by the same amount. For example, the experimental radioactive counts of the control RNA were reduced by 12%, to achieve a ratio of 0.50. This same 12% reduction was then applied to the values for the corresponding reporter RNA (unspliced (us) and spliced (s)) bands in the same lane. Similar corrections were performed for other RNAse protection data.

RESULTS

Polyadenylated H2a mRNA Accumulates Efficiently in the Cytoplasm, but Human β-globin cDNA Transcripts do not To determine whether there are sequences within the histone H2a gene that function to help in cytoplasmic RNA accumulation, a plasmid construct H-p(A) was first made that expresses polyadenylated histone mRNAs (FIG. 1). H-p(A) contains the mouse histone H2a transcribed region (nucleotides −2 to +496 relative to the histone transcription start site) but lacks the 3' end stem-loop and other histone 3' end processing sequences. Transcription is driven by the CMV promoter, and mRNA 3' ends are generated by polyadenylation. This clone allowed the uncoupling of expression of the H2a gene from cell cycle regulation, as transcription and histone 3' end processing (not polyadenylation) have been shown to be the key targets for the cell cycle regulation (Harris et al., *Mol Cell Biol* 11:2416–24 (1991); Sittman et al., *Proc Natl Acad Sci USA* 80:1849–53 (1983)). To analyze the intracellular distribution of polyadenylated histone mRNAs, H-p(A) was transfected into COS7 cells. Nuclear and cytoplasmic RNAs were extracted 48 hours after transfection, and examined by quantitative RNAse protection assays. As a control, the level of mRNA produced from a human β-globin cDNA expression vector was examined in a parallel experiment.

The cytoplasmic accumulation of the globin cDNA transcripts is extremely low, suggesting that nuclear export of these RNAs is poor. In contrast, mRNAs transcribed from the H-p(A) construct accumulate in the cytoplasm to a level 23-times that of β globin messages, indicating that export of these transcripts is much more efficient compared to that of the globin cDNA transcripts. The size of the protected band indicates that the histone mRNA is polyadenylated at the predicted site. RNAse protection assays using probes complementary to other regions of the histone gene revealed that no cryptic splicing had occurred. The above results therefore raised the possibility that the H2a transcribed region may contain cis-acting sequences that allow efficient cytoplasmic accumulation of intronless or unspliced mRNAs.

Sequences within the H2a gene permit efficient cytoplasmic accumulation of human β-globin cDNA transcripts.

To identify putative cis-acting sequences responsible for intronless mRNA transport, a chimeric gene H-βG was created in which the 498-base pair H2a transcribed region was inserted into the 5' untranslated region of a human β-globin cDNA clone (FIG. 2). It was then determined whether this sequence could rescue the defects in cytoplasmic accumulation of the globin cDNA transcripts. The H-βG plasmid was introduced into COS7 cells by transfection and the subcellular distribution of RNAs was measured by RNAse protection assays. Results reveal that inclusion of the histone sequences elevated the cytoplasmic accumulation of the globin RNA by 25-fold. Insertion of the same histone sequences upstream of the β-globin promoter region did not have such an effect. These results strongly suggested the presence of cis-acting sequences within the H2a transcribed region that enable efficient cytoplasmic accumulation of unspliced mRNAs.

Identification of a functional element that facilitates cytoplasmic accumulation of intronless transcripts.

Figure 3B:
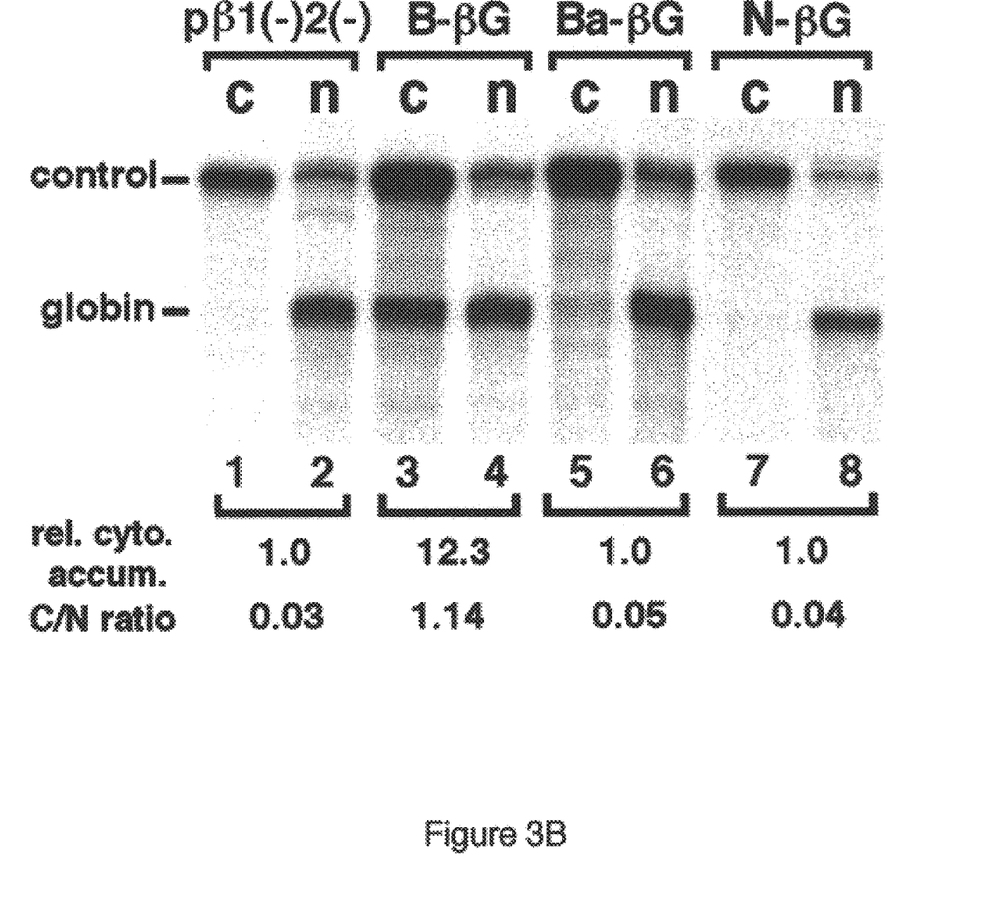

Based on the findings described above, a search was performed for a smaller cis-acting sequence capable of enhancing the cytoplasmic accumulation of unspliced mRNAs. Using PCR and cloning techniques, a 101-base pair sequence (fragment B) within the H2a coding region was defined that has such a function, while a fragment from another region does not. As shown in FIG. 3A, three constructs were made by inserting PCR fragments into the 5' untranslated region of the globin cDNA gene. In B-βG and Ba-βG, fragment B was inserted in the sense and antisense orientations, respectively. Fragment B does not contain any AUG codon that might confuse results by inducing nonsense-mediated mRNA decay within the nucleus. In B-βG, the 75-base pair histone sequence (fragment N) was inserted in the sense orientation. Results from an RNAse protection assay with RNAs prepared from the transfected cells (FIG. 3B) show that fragment B in the sense orientation increased the cytoplasmic accumulation of the globin RNA by approximately 12-fold. This effect is orientation-dependent, since the same sequence inserted in the opposite direction had no effect on the intracellular distribution of the globin RNA. This effect is also specific, as insertion of the sequence from another region of the H2a gene did not change the cytoplasmic accumulation of the globin RNA. In additional work, it has been shown that multiple tandem copies of this element work significantly better than a single copy. Thus, this invention also pertains to nucleotide constructs comprising more than one copy of the cis-acting cellular or non-viral element described herein; the multiple copies can be linked to each other directly or by means of a linker comprising one or more nucleotides.

The histone sequence can replace Rev and RRE for the cytoplasmic accumulation of unspliced HIV-1-related mRNA.

Figure 5:
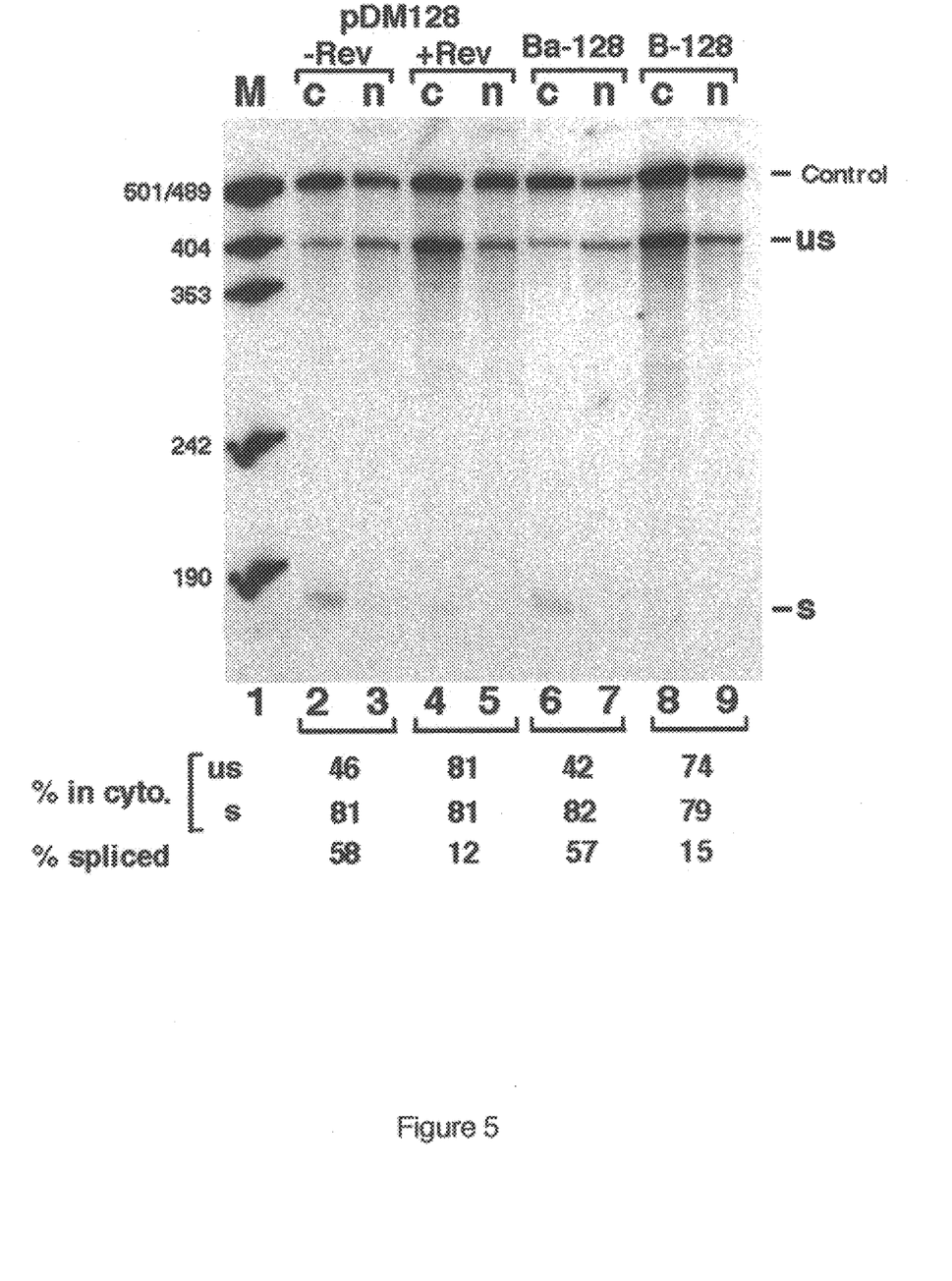
FIG. 5 is a photograph of the results of RNAse protection assays of RNAs prepared from cells transfected with the indicated plasmids and the quantitation of the fraction of either unspliced (us) or spliced (s) RNA that was detected in the cytoplasm of cells transfected with the indicated plasmids, as well as the percentage of total RNA that was spliced. "+Rev" indicates with co-transfection of the Rev-expressing vector; and "−Rev" indicates without co-transfection of the Rev-expression vector. "M" indicates molecular size markers (501/489, 404, 353, 242 and 190 bp, respectively, from the top). "C" indicates cytoplasmic RNA and "N" indicates nuclear RNA. The control was RNA from the co-transfected control plasmid pH-XβG.

To further understand how this sequence works, fragment B was inserted into the intron region of an HIV-1-based reporter construct pDM128 (FIG. 4). In B-128 and Ba-128, the fragment was inserted in the sense and antisense orientations, respectively. It has been shown that efficient cytoplasmic accumulation of unspliced mRNAs transcribed from subgenomic HIV-1 constructs is generally dependent on the presence of a functional Rev protein (Peterlin et al., *Proc Natl Acad Sci U.S.A.* 83:9734–9738 (1986); Harris et al., *Mol Cell Biol* 11:2416–24 (1991); Sittman et al., *Proc Natl Acad Sci USA* 80:1849–53 (1983); Malim et al., *Nature* 338:254–257 (1989)). Consistent with this, the cytoplasmic accumulation of the unspliced species transcribed from the reporter construct is significantly augmented when Rev is expressed (FIG. 5). In addition, the increased level of unspliced species is accompanied by a decreased level of spliced species. These results are in agreement with observations from other groups (Bray et al., *Proc. Natl. Acad. Sci. USA* 91:1256–1260 (1994); Peterlin et al., *Proc Natl Acad Sci U.S.A.* 83:9734–9738 (1986); Malim & Cullen, *Mol. Cell. Biol.* 13:6180–6189 (1993)). Intriguingly, in the absence of Rev, the presence of the 101-base pair sequence in the reporter construct leads to increased cytoplasmic accumulation of the unspliced species and a concomitant decrease in the level of the spliced species. These results suggest that the histone sequence may act to enhance the nuclear export of the unspliced RNAs and to suppress splicing as well. Like RRE, this sequence is functional only when placed in the sense orientation. Since the presence of this sequence in the globin cDNA or in the HIV-1-related gene construct did riot significantly alter mRNA half-lives in either the nucleus or the cytoplasm, it is thus unlikely that it acts at the RNA stability level. That the histone sequence can functionally mimic RRE and acts in an orientation-dependent manner is consistent with the view that it may function at the posttranscriptional level.

Sequences Contained within the H2a Gene Enhance Polyadenylation

Evidence exists that introns facilitate polyadenylation of mRNAs, and thus the question of whether sequences contained within the histone gene have the similar effect was addressed. To this end, plasmids pβ1(-)2(-) and H-βG were each transfected into COS7 cells, and RNAse protection assays with RNAs extracted from the transfected cells were performed. In addition, similar constructs were used which contained the HSV-1 TK element, or the HBV element. A riboprobe complementary to the poly(A) region was used to detect the processed (polyadenylated) and unprocessed (readthrough) RNA transcripts. Thus, the relative efficacy of 3'-end processing of these transcripts can be determined by the ratio between the processed and the unprocessed species. The majority (73%) of the mRNAs transcribed from the globin cDNA construct are unprocessed. More importantly, the unprocessed species are exclusively retained in the nucleus. This indicates that the efficiency of 3'-end processing of mRNAs produced from the cDNA is extremely poor. Importantly, of the 27% of the globin transcripts that are correctly processed, few, if any, could be detected in the cytoplasm. Interestingly, the presence of the histone sequence in the globin cDNA leads to dramatic improvement in both the 3'-end processing efficacy and mRNA export. Thus, now 95% of the transcripts were correctly processed and of these, 74.5% were exported to the cytoplasm. These results thus suggest that the low levels of the globin cDNA RNA in the cytoplasm observed are due to both a transport block and to poor 3'-end processing efficiency. Remarkably and unexpectedly, the HBV and TK elements work in precisely the same way, raising the possibility that diverse "transport" elements work in analogous ways. It is possible that a general feature of mRNA transport elements is not only transport, but also the entire collection of phenotypes including splicing inhibition, 3'-end processing enhancement and mRNA transport.

EQUIVALENTS

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. An isolated cis-acting cellular nucleic acid molecule from a histone gene, wherein said nucleic acid molecule performs one or more functions selected from the group consisting of:
   a) suppressing splicing of an RNA transcript;
   b) enhancing 3' end formation of an RNA transcript;
   c) facilitating transport of fully unspliced, alternatively spliced or partially spliced RNA from a cell nucleus to the cytoplasm of the cell; and
   d) facilitating transport of RNA from intronless DNA from a cell nucleus to the cytoplasm of the cell,
and wherein said nucleic acid molecule is operably linked to a second nucleic acid molecule which is not from a histone gene.

2. An isolated cis-acting cellular nucleic acid molecule according to claim 1, wherein said histone gene is H2a.

3. An isolated cis-acting cellular nucleic acid molecule according to claim 1, wherein said nucleic acid molecule is a portion of said histone gene.

4. An isolated cis-acting cellular nucleic acid molecule according to claim 1, wherein said histone gene comprises SEQ ID NO: 1.

5. An isolated cis-acting cellular nucleic acid molecule according to claim 2, wherein said nucleic acid molecule is a portion of said historic gene.

6. An isolated cis-acting cellular nucleic acid molecule according to claim 2, wherein said histone gene is murine H2a.

7. An isolated cis-acting cellular nucleic acid molecule according to claim 3, wherein said portion consists essentially of nucleotides 201–301 of SEQ ID NO: 1.

8. An isolated cis-acting cellular nucleic acid molecule from a histone gene, wherein said nucleic acid molecule is a portion of said histone gene and wherein said nucleic acid molecule performs one or more functions selected from the group consisting of:
   a) suppressing splicing;
   b) enhancing 3' end formation;

c) facilitating transport of partially spliced, alternatively spliced or fully unspliced RNA from a cell nucleus to the cytoplasm of the cell; and d) facilitating transport of RNA from intronless DNA from a cell nucleus to the cytoplasm of the cell.

9. An isolated cis-acting cellular nucleic acid molecule according to claim 8, wherein said histone gene is H2a.

10. An isolated cis-acting cellular nucleic acid molecule according to claim 8, wherein said histone gene comprises SEQ ID NO: 1.

11. An isolated cis-acting cellular nucleic acid molecule according to claim 9, wherein said histone gene is murine H2a.

12. An isolated cis-acting cellular nucleic acid molecule according to claim 8, wherein said portion consists essentially of nucleotides 201–301 of SEQ ID NO: 1.

13. An expression vector comprising a cis-acting cellular nucleic acid molecule from a histone gene, wherein said nucleic acid molecule performs one or more functions selected from the group consisting of:

a) suppressing splicing of an RNA transcript;

b) enhancing 3' end formation of an RNA transcript;

c) facilitating transport of fully unspliced, alternatively spliced or partially spliced RNA from a cell nucleus to the cytoplasm of the cell; and d) facilitating transport of RNA from intronless DNA from a cell nucleus to the cytoplasm of the cell, operably linked to a regulatory sequence and to a second nucleic acid molecule which is not from a histone gene.

14. An expression vector comprising a cis-acting cellular nucleic acid molecule from a histone gene, wherein said nucleic acid molecule is a portion of said histone gene and wherein said nucleic acid molecule performs one or more functions selected from the group consisting of:

a) suppressing splicing;

b) enhancing 3' end formation;

c) facilitating transport of partially spliced, alternatively spliced or fully unspliced RNA from a cell nucleus to the cytoplasm of the cell; and d) facilitating transport of RNA from intronless DNA from a cell nucleus to the cytoplasm of the cell, operably linked to a regulatory sequence.

15. An isolated cis-acting cellular nucleic acid molecule, wherein said nucleic acid molecule is less than about 515 nucleotides in length and wherein said nucleic acid molecule performs one or more functions selected from the group consisting of:

a) suppressing splicing of an RNA transcript;

b) enhancing 3' end formation of an RNA transcript;

c) facilitating transport of fully unspliced, alternatively spliced or partially spliced RNA from a cell nucleus to the cytoplasm of the cell; and d) facilitating transport of RNA from intronless DNA from a cell nucleus to the cytoplasm of the cell, and further wherein said nucleic acid molecule is operably linked to a second nucleic acid molecule which is not from the same gene as the cis-acting cellular nucleic acid molecule.

16. An expression vector comprising a cis-acting cellular nucleic acid molecule, wherein said nucleic acid molecule is less than about 515 nucleotides in length and wherein said nucleic acid molecule performs one or more functions selected from the group consisting of:

a) suppressing splicing of an RNA transcript;

b) enhancing 3' end formation of an RNA transcript;

c) facilitating transport of fully unspliced, alternatively spliced or partially spliced RNA from a cell nucleus to the cytoplasm of the cell; and d) facilitating transport of RNA from intronless DNA from a cell nucleus to the cytoplasm of the cell, and further wherein said nucleic acid molecule is operably linked to a second nucleic acid molecule which is not from the same gene as the cis-acting cellular nucleic acid molecule.

17. An isolated cis-acting cellular nucleic acid molecule, wherein said nucleic acid molecule is less than about 515 nucleotides in length and wherein said nucleic acid molecule performs one or more functions selected from the group consisting of:

a) suppressing splicing of an RNA transcript;

b) enhancing 3' end formation of an RNA transcript;

c) facilitating transport of fully unspliced, alternatively spliced or partially spliced RNA from a cell nucleus to the cytoplasm of the cell; and d) facilitating transport of RNA from intronless DNA from a cell nucleus to the cytoplasm of the cell.

18. An expression vector comprising a cis-acting cellular nucleic acid molecule, wherein said nucleic acid molecule is less than about 515 nucleotides in length and wherein said nucleic acid molecule performs one or more functions selected from the group consisting of:

a) suppressing splicing of an RNA transcript;

b) enhancing 3' end formation of an RNA transcript;

c) facilitating transport of fully unspliced, alternatively spliced or partially spliced RNA from a cell nucleus to the cytoplasm of the cell; and d) facilitating transport of RNA from intronless DNA from a cell nucleus to the cytoplasm of the cell, and further wherein said nucleic acid molecule is operably linked to a regulatory sequence.

19. An expression vector according to claim 18, further comprising a second nucleic acid molecule, which is not from the same gene as the cis-acting cellular nucleic acid molecule, operably linked to said regulatory sequence.

* * * * *